United States Patent [19]
Ota et al.

[11] Patent Number: 5,021,186
[45] Date of Patent: Jun. 4, 1991

[54] CHLOROISOCYANURIC ACID COMPOSITION HAVING STORAGE STABILITY

[75] Inventors: Masanori Ota; Masafumi Aoki; Masashi Nakamura; Kenichi Mizusawa; Kumi Kasahara, all of Funabashi, Japan

[73] Assignee: Nissan Chemical Industries, Ltd., Tokyo, Japan

[21] Appl. No.: 326,741

[22] Filed: Mar. 21, 1989

[30] Foreign Application Priority Data

Mar. 25, 1988 [JP] Japan ................................. 63-70990
Mar. 25, 1988 [JP] Japan ................................. 63-70991

[51] Int. Cl.$^5$ ........................ C09K 15/00; C01B 7/00
[52] U.S. Cl. ........................ 252/186.35; 252/187.34; 210/755
[58] Field of Search ................. 252/186.35, 187.34; 210/755

[56] References Cited

U.S. PATENT DOCUMENTS

| 3,061,549 | 10/1962 | Dickey ................. 252/186.35 X |
| 4,124,499 | 11/1978 | Hobbs et al. ................. 210/667 |
| 4,334,610 | 6/1982 | Ota et al. ................. 206/205 |
| 4,389,325 | 6/1983 | Eng et al. ................. 252/187.34 X |
| 4,715,983 | 12/1987 | Ota et al. ................. 252/186.35 |

Primary Examiner—John S. Maples
Assistant Examiner—Greg M. Sweet
Attorney, Agent, or Firm—Oliff & Berridge

[57] ABSTRACT

The present invention relates to a chloroisocyanuric acid composition having stability during storage characterized by formulating, as a main component, 1 to 200 parts by weight of at least one aluminum sulfate selected from aluminum sulfate ($Al_2(SO_4)_3 \cdot XH_2O$, $X=0$ to 18), potassium alum ($KAl(SO_4)_2 \cdot XH_2O$, $X=0$ to 12) and sodium alum ($NaAl(SO_4)_2 \cdot XH_2O$, $X=0$ to 12) in 100 parts by weight of trichloroisocyanuric acid and/or dichloroisocyanuric acid.

4 Claims, No Drawings

CHLOROISOCYANURIC ACID COMPOSITION HAVING STORAGE STABILITY

BACKGROUND OF THE INVENTION

1. Filed of the Invention

The present invention relates to a chloroisocyanuric acid composition having excellent stability during storage, comprising as the main components trichloroisocyanuric acid and/or dichloroisocyanuric acid, which is hydrolyzed in water to release active chlorine used for sterilization and bleaching and washing.

2. Description of the Prior Art

Chloroisocyanuric acids have been used from old as over wide fields as sterilizers, disinfectants or algicides for pool water, sewage, industrial water, cooling water, etc. or bleaching detergents for fibers, etc. As the chloroisocyanuric acid, there are known trichloroisocyanuric acid, dichloroisocyanuric acid, sodium dichloroisocyanurate, sodium dichloroisocyanurate dihydrate and potassium dichloroisocyanurate, etc.

The chloroisocyanuric acids have been provided in many preparatory forms such as powders, granules, spheres, tablets, etc. Further for the purpose of controlling dissolution in water, investigations have been made not only on shape but on preparations designed in their formulations.

However, chloroisocyanuric acids tend to generate chlorine gas or nitrogen chloride gas during storage or upon use, especially in a wet state and tend to cause reduction in effective ingredients, deterioration of packaging materials, etc. In addition, where alkaline compounds are formulated together with chloroisocyanuric acids, the acids are stable in a dry state but extremely vigorously decomposed in a wet state to accelerate generation of chlorine gas or nitrogen chloride gas. Furthermore, chloroisocyanuric acids are strong oxidizing agents so that when they are formulated together with other chemicals, the chloroisocyanuric acids per se often decompose to generate chlorine gas or nitrogen chloride gas. Among the chloroisocyanuric acids described above, the phenomenon is particularly remarkable with trichloroisocyanuric acid and dichloroisocyanuric acid.

As described above, mixing of the chloroisocyanuric acids with moisture or various compounds accelerates self decomposition so that it is not easy to determine the formulation compatible with the chloroisocyanuric acids. Accordingly, studies have been considerably made on properties of the chloroisocyanuric acids. For example, in order to prevent generation of gas by decomposition of the chloroisocyanuric acids, there have been proposed some reports or proposals that it is effective to reduce the moisture content in the product or to completely shield the moisture coming from the outside during storage, etc. However, any of them is unsatisfactory. For example, to manufacture the absolute anhydrous products is difficult in such a degree that it is impossible to industrially manufacture them. Even though metals are used as packaging materials that can be completely shielded from the air, decomposed gas sealed in would gradually accumulate during storage over long periods of time to cause corrosion of a wall, deformation or breakage, etc. of a container due to an increased pressure.

It has also been proposed to cover the surface of chloroisocyanuric acids with a film of inert substances, for example, paraffin wax or polyvinyl alcohol. However, the effect is not sufficient, as in the methods described above. Further when this is used for sterilization of pool water, oils are undesirably supplied in pool water. Furthermore, as is described in U.S. Pat. No. 3,061,549, there is a method in which the chloroisocyanuric acids are stored in a container made of paper board having coated thereon an alkali metal silicate. However, the container made of paper board coated with the alkali metal silicate is deteriorated in a short period of time but does not withstand storage over long periods and cannot sufficiently prevent decomposition of the chloroisocyanuric acid. It is also difficult to store the chloroisocyanuric acids over long periods in such a state that the acids are not changed.

Recently, some new proposals have been made. For example, in U.S. Pat. No. 4,334,610, there is proposed a method for stably storing the chloroisocyanuric acids in which compounds such as calcium oxide, sodium phosphate, ferrous oxide, magnesium oxide, zeolite, melamine, anmeline, etc. are charged in a porous bag having gas permeability and the chloroisocyanuric acids are packed in a storage container. However, this method encounters defects that the porous bag obstructs the opening of the storage container or the porous bag is sometimes broken, etc. when the chloroisocyanuric acids are taken out of the container.

Further in U.S. Pat. No. 4,389,325, there is proposed a method in which specific synthetic zeolite (main ingredient: aluminosilicate) is used to prevent the generation of chlorine gas. However, no remarkable effect is necessarily obtained.

With respect to the storage stability, the present inventors already filed an application directed to stabilizers comprising allophane compounds and activated charcoal, which matured into U.S. Pat. No. 4,715,983. The stabilizers are surely good but because activated charcoal is present, the product is colored black when mixed with the chloroisocyanuric acids. The coloration reduces commercial value of goods and the stabilizers should be put in a porous bag and provided for use. When the same problem as in U.S. Pat. No. 4,334,610 supra encounters.

In addition, trichloroisocyanuric acid and dichloroisocyanuric acid are extremely difficultly soluble in water, as compared to alkali metal salts of dichloroisocyanuric acid which is another chloroisocyanuric acid. However, trichloroisocyanuric acid and dichloroisocyanuric acid have the active chlorine contents as high as 90% or more and 70% or more, respectively, as compared to other chloroisocyanuric acids. Utilizing low solubility in water, trichloroisocyanuric acid and dichloroisocyanuric acid have been used in large quantities as sterilizers, disinfectants and slime controlling agents for pool water, sewage from septic tanks, industrial water or cooling water. Depending upon the quantity of water used or degree of pollution of water, or in the case of removing algae in water, removing ammoniacal nitrogen and further in the case of starting use of pool, etc., rapid dissolution and enhancement of active chlorine concentration is necessary; however, trichloroisocyanuric acid and dichloroisocyanuric acid themselves have the problem that their dissolution rate in water is extremely slow.

In order to improve the solubility of trichloroisocyanuric acid, various proposals have been made to solve the problem. For example, Japanese Patent Laid-open Publication No. Sho 54-160730 (160730/1979) utilizes that tablets prepared from trichloroisocyanuric acid and sodium cyanurate as well as a disintegration auxiliary are immediately disintegrated in water. Japanese Patent Laid-open Publication No. Sho58-46003 (46003/1983) proposes a chloroisocyanurate composition comprising trichloroisocyanuric acid, an alkali metal salt of dichloroisocyanuric acid and anhydrous sodium sulfate or sodium chloride which possesses rapid and long acting properties. Furthermore, the present inventors have proposed a composition of trichloroisocyanuric acid, cyanuric acid and an alkali metal phosphate (Japanese Patent Laid-open Publication No. Sho 58-59904 (59904/1983)) or a composition obtained by formulating isocyanuric acid and magnesium oxide or magnesium isocyanurate in trichloroisocyanuric acid (Japanese Patent Publication No. Sho 61-41883 (41883/1986)). However, trichloroisocyanuric acid and dichloroisocyanuric acid are more reactive than other chloroisocyanuric acids and sensitive particularly to moisture and alkaline substances. Therefore, when they are exposed to high humidity or mixed with alkaline substances, chlorine gas and nitrogen chloride gas tend to generate, resulting in reduction of effective ingredients and deterioration of packaging materials, etc. Thus, the above proposals also encounter the problem that attention should be paid to control during storage and upon use.

SUMMARY OF THE INVENTION

In order to solve the foregoing problems, the present inventors have made intensive studies. As a result, it has been found that when an aluminum sulfate salt is formulated, the resulting composition can stabilize trichloroisocyanuric acid and dichloroisocyanuric acid which are the most unstable chloroisocyanuric acids, even in a wet state and further that dissolution is uniform and tablets prepared from the composition of the present invention provides a more rapid dissolution rate than tablets prepared from trichloroisocyanuric acid and/or dichloroisocyanuric acid alone.

That is, the present invention relates to a chloroisocyanuric acid composition having stability during storage characterized by formulating, as a main component, 1 to 200 parts by weight of at least one aluminum sulfate salt selected from aluminum sulfate ($Al_2(SO_4)_3 \cdot XH_2O$, $X=0$ to 18), potassium alum ($KAl(SO_4)_2 \cdot XH_2O$, $X=0$ to 12) and sodium alum ($NaAl(SO_4)_2 \cdot XH_2O$, $X=0$ to 12) in 100 parts by weight of trichloroisocyanuric acid and/or dichloroisocyanuric acid.

DETAILED DESCRIPTION OF THE INVENTION

The chlorisocyanuric acid used in the present invention includes trichloroisocyanuric acid and/or dichloroisocyanuric acid which is in the form of powder or granule.

The aluminum sulfate salt used in the present invention is at least one compound selected from aluminum sulfate ($Al_2(SO_4)_3 \cdot XH_2O$, $X=0$ to 18), potassium alum ($KAl(SO_4)_2 \cdot XH_2O$, $X=0$ to 12) and sodium alum ($NaAl(SO_4)_2 \cdot XH_2O$, $X=0$ to 12). Of these aluminum sulfate salts, preferred examples are those having the following crystal water, i.e., hydrated aluminum sulfate ($Al_2(SO_4)_3 \cdot XH_2O$, $X=6$ to 18), hydrated potassium alum ($KAl(SO_4)_2 \cdot XH_2O$, $X=6$ to 12) and hydrated sodium alum ($NaAl(SO_4)_2 \cdot XH_2O$, $X=6$ to 12). Especially, aluminum sulfate 18 hydrate, potassium alum 12 hydrate and sodium alum 12 hydrate are preferable.

The amount of the aluminum sulfate salt used in the present invention is 1 to 200 parts by weight, preferably 2 to 100 parts by weight, based on 100 parts by weight of the aforesaid chloroisocyanuric acid. With less than 1 part by weight, the stabilizing effect of the chloroisocyanuric acid is poor. When the amount exceeds 200 parts by weight, the effective chlorine concentration decreases and such is not preferred. As the formulation, it is enough to mix granules or powders of chloroisocyanuric acid with powders or crystals of aluminum sulfate salt. In this case, a particle size of the aluminum sulfate salt to be formulated is preferably not greater than 2000 μm.

The mixture of the chloroisocyanuric acid and the aluminum sulfate salt may also be prepared by adding aluminum sulfate salt or a concentrated aqueous solution or slurry of the aluminum sulfate salt to the chloroisocyanuric acid in a slurry state in an aqueous medium obtained at steps of producing chloroisocyanuric acid, mixing them, dehydrating and drying.

Anhydrous aluminum sulfate salts are stable when formulated in trichloroisocyanuric acid and/or dichloroisocyanuric acid but when tableted, the tablets encounter problems to cause cracking or collapse upon use or to be uniformly dissolved only with difficulty when used by filling the tablets in layers in a cylindrical holder. Therefore, when the composition is used in the form of tablets, hydrated aluminum sulfate ($Al_2(SO_4)_3 \cdot XH_2O$, $X=6$ to 18), hydrated potassium alum ($KAl(SO_4)_2 \cdot XH_2O$, $X=6$ to 12) and hydrated sodium alum ($NaAl(SO_4)_2 \cdot XH_2O$, $X=6$ to 12) described above are preferred. Particularly preferred are aluminum sulfate 18 hydrate, potassium alum 12 hydrate and sodium alum 12 hydrate.

The composition of the present invention comprising the chloroisocyanuric acid and the aluminum sulfate salt may also contain other optional additives so long as the objects of the present invention are achieved. For example, isocyanuric acid as an extender, talc, boric acid, stearic acid salt, etc. as an excipient may be added to the composition.

The preparation form of the chloroisocyanuric acid composition of the present invention may be any form of powders, granules, spheres, tablets and the like. Tableting may be carried out in a conventional fashion.

The present invention is particularly markedly effective for stabilizing trichloroisocyanuric acid and dichloroisocyanuric acid during storage which are more unstable of the alkali metal salt of dichloroisocyanuric acid among the chloroisocyanuric acids. The resulting composition is stable and characteristic of minimized generation of chlorine gas and nitrogen chloride gas, as compared to the case where the aluminum sulfate salt is not formulated in trichloroisocyanuric acid and dichloroisocyanuric acid. In addition, the dissolution is uniformly effected and more rapid than in tablets prepared from trichloroisocyanuric acid and/or dichloroisocyanuric acid alone. Further when the tablets are filled in layers in a cylindrical holder and provided for use (in a septic tank, etc.), cracking, swelling, collapse, etc. of the tablets do not occur so that problems of clotting the medical tube with the tablets, etc. are not caused. Thus, there is no problem to dissolve the chloroisocyanuric acid in waste water to be treated so that the composition is effective for supplying chlorine in a definite concentration. Hereafter the present invention is described in more detail by referring to the examples and comparative examples.

EXAMPLES 1 THROUGH 11 AND COMPARATIVE EXAMPLES 1 THROUGH 8

Raw materials shown in Table 1 were mixed in a dry state. According to the following methods for evaluating stability of the resulting compositions during storage, chlorine gas and nitrogen chloride gas generated in a dry state and in a wet state were measured. The results are also shown in Table 1.

A particle diameter of each of trichloroisocyanuric acid (abbreviated as TCCA) and dichloroisocyanuric acid (abbreviated as DCCA) used in as follows.

| TCCA | powder | 80 to 500 μm | (100 μm in average) |
| TCCA | powder | 80 to 500 μm | (100 μm in average) |
| DCCA | powder | 80 to 500 μm | (100 μm in average) |
| TCCA | granule | 400 to 1600 μm | (1000 μm in average) |
| DCCA | granule | 400 to 1600 μm | (1000 μm in average) |

(Evaluation of stability during storage)

A. STABILITY IN A DRY STATE

In a three-necked glass-made flask having an inner volume of 500 ml, 30 g of a sample in the form of powders or granules was charged. The first port was sealed with a rubber stopper. A glass stopper with a valve was mounted to the second and third ports, respectively, which were made closed. The flask was stored for 24 hours in a thermostat at 40° C. Then, a conduit for dry nitrogen gas was connected with the second port and a conduit leading to 50 ml of 0.5% sodium hydroxide aqueous solution was connected with the third port. Immediately after the termination of storage, both valves were opened. Dry nitrogen was introduced through the second port and exhausted gas from the third port was led to the sodium hydroxide aqueous solution to absorb the gas generated by decomposition. After the gas was blown, 0.2 g of potassium iodide was added to the sodium hydroxide aqueous solution. The isolated iodine under sulfuric acid-acidic conditions was titrated using starch as an indicator to determine the effective chlorine amount absorbed in the sodium hydroxide aqueous solution. The amount of the effective chlorine was made the total amounts of the chlorine gas and nitrogen chloride gas generated from the chloroisocyanuric acid composition in a dry state.

B. STABILITY IN A WET STATE

In the aforesaid three-necked flask, 30 g of a sample in the form of powders or granules was charged and 10 ml of hot water at 40° C. was sprinkled over the samples. After storage for an hour in a thermostat at 40° C., the chlorine gas and nitrogen chloride gas generated were led to the sodium hydroxide aqueous solution and an amount of gas generated from the chloroisocyanuric acid composition in a wet state was determined in a manner similar to the item A above.

EXAMPLE 12

As the chloroisocyanuric acid, 70 g of dichloroisocyanuric acid powders was used and mixed with 30 g of sodium alum 12 hydrate as the aluminum sulfate salt. To the mixture was added 60 ml of distilled water. The resulting mixture was kneaded with a kneader and then filtered to give a wet cake. The cake was dried in a fluidized state at an exhaust gas temperature of 60° C. for 30 minutes. Using 30 g of the resulting powders, evaluation was performed in a manner similar to Examples 1 to 11. The results are shown in Table 1.

EXAMPLE 13

Evaluation was performed in a manner similar to Example 12 except that the dichloroisocyanuric acid and sodium alum 12 hydrate in Example 12 were changed to trichloroisocyanuric acid powders and potassium alum 12 hydrate powders, respectively.

EXAMPLES 14 THROUGH 23 AND COMPARATIVE EXAMPLES 10 THROUGH 19

Raw materials for formulation described in Table 2 were mixed in a dry state and tablets were prepared these mixtures according to the tableting method described below. With respect to the resulting tablets, an amount of chlorine gas and nitrogen chloride gas generated were measured in a dry state and in a wet state, in a manner similar to the method described above. Furthermore, a dissolution rate and active chlorine concentration after 8 hours passed were determined by the following evaluation methods. The results are also shown in Table 2.

In Examples 22 and 23, 3.0 g of orthoboric acid (powders) was formulated in addition to the aluminum sulfate salt.

C. METHOD FOR TABLETING

Raw materials for formulation described in Table 1 were uniformly mixed. The resulting composition, 30 g, was filled in a motar having a diameter of 35 mm and a pestle was put thereon. A pressure was applied under a surface pressure of about 400 kg/cm² with a hydraulic press to effect compression molding. Thus, a tablet having a diameter of 35 mmφ, a thickness of 19 mm and a density of 1.60 to 1.80 g/cm² was obtained.

D. DISSOLUTION RATE OF TABLET AND METHOD FOR DETERMINING ACTIVE CHLORINE CONCENTRATION

Tap water (ground water) at 17±1° C. was continuously passed through a water tank having a height, width and depth of 400×400×100 mm in a rate of 3 liters/min. The liquid surface was overflown to keep the level constant. A stainless metal mesh stand of 4 mesh (mesh opening of 4.7 mm) was put at the depth of 50 mm below the liquid surface and each tablet obtained by the molding method present invention was put thereon. Eight hours after passing water therethrough, a weight of the remaining tablet was measured after drying with hot dry air and the weight of the dissolved tablet was calculated therefrom. At the time when the remaining tablet was withdrawn, the active chlorine concentration in running water was measured by the ortho-toluidine method. The results are shown in Table 2. In Comparative Example 11 to 19, the tablets were cracked or collapsed so that it was impossible to measure.

TABLE 1

(powder, granule)

| | Composition | | | | Amount of Chlorine or Nitrogen Chloride Gas mg | |
|---|---|---|---|---|---|---|
| | Chloroisocyanuric Acid g | | Aluminum Sulfate Salt g | Form | Dry State | Wet State |
| Comp. Ex. 1 | TCCA (powder) | 21.0 | — | | Powder | 0.31 | 24.9 |
| Ex. 1 | TCCA (powder) | 27.0 | Potassium alum anhydride (powder) | 3.0 | Powder | 0.12 | — |
| Ex. 2 | TCCA (powder) | 21.0 | Potassium alum anhydride (powder) | 9.0 | Powder | 0.09 | 11.1 |
| Ex. 3 | TCCA (powder) | 21.0 | Sodium alum anhydride (powder) | 9.0 | Powder | 0.11 | — |
| Ex. 4 | TCCA (powder) | 21.0 | Sodium aluminum anhydride (powder) | 9.0 | Powder | 0.07 | — |
| Ex. 5 | TCCA (powder) | 21.0 | Potassium alum 12 hydrate (powder) | 9.0 | Powder | 0.05 | 10.3 |
| Ex. 6 | TCCA (powder) | 21.0 | Sodium alum 12 hydrate (powder) | 9.0 | Powder | 0.12 | — |
| Ex. 7 | TCCA (powder) | 21.0 | Aluminum sulfate 18 hydrate (powder) | 9.0 | Powder | 0.28 | 9.7 |
| Comp. Ex. 2 | TCCA (granule) | 21.0 | — | | Granule | 0.24 | 22.9 |
| Ex. 8 | TCCA (granule) | 28.5 | Sodium alum 12 hydrate (crystal) | 1.5 | Granule | 0.14 | 9.4 |
| Ex. 9 | TCCA (granule) | 24.0 | Potassium alum 12 hydrate (powder) | 6.0 | Granule | 0.05 | 8.9 |
| Ex. 10 | TCCA (granule) | 25.5 | Sodium sulfate 18 hydrate (powder) | 4.5 | Granule | 0.23 | 9.1 |
| Comp. Ex. 3 | TCCA (granule) | 21.0 | Potassium alum 12 hydrate (powder) | 0.2 | Granule | 0.30 | 15.1 |
| Comp. Ex. 4 | TCCA (granule) | 21.0 | Sodium sulfate 10 hydrate (powder) | 9.0 | Granule | 33.5 | ≧50 |
| Comp. Ex. 5 | TCCA (granule) | 21.0 | Magnesium sulfate 7 hydrate (powder) | 9.0 | Granule | 17.5 | ≧50 |
| Comp. Ex. 6 | TCCA (granule) | 21.0 | Magnesium chloride 2 hydrate (powder) | 9.0 | Granule | 27.1 | ≧50 |
| Comp. Ex. 7 | DCCA (powder) | 21.0 | — | | Powder | 0.19 | 6.7 |
| Ex. 11 | DCCA (powder) | 21.0 | Potassium alum 12 hydrate (powder) | 9.0 | Powder | 0.08 | 3.2 |
| Comp. Ex. 8 | DCCA (granule) | 21.0 | — | | Granule | 0.17 | 6.0 |
| Ex. 12 | DCCA (powder) | 21.0 | Sodium alum 12 hydrate (crystal) | 9.0 | Powder | 0.03 | 2.6 |
| Ex. 13 | TCCA (powder) | 21.0 | Potassium alum 12 hydrate (powder) | 9.0 | Powder | 0.08 | 7.8 |

TCCA: trichloroisocyanuric acid
DCCA: dichloroisocyanuric acid

TABLE 2

(tablet)

| | Composition | | | Amount of Chlorine or Nitrogen Chloride Gas mg | | Dissolution Rate g/30 g/ 8 hr | Active Chlorine Concentration 8 Hrs. After ppm | Appearance |
|---|---|---|---|---|---|---|---|---|
| | Chloroisocyanuric Acid g | | Aluminum Sulfate Salt g | Dry State | Wet State | | | |
| Ex. 14 | TCCA | 21.0 | Potassium alum | 9.0 | 0.05 | 10.4 | 14.2 | 6.2 | No collapsed |

TABLE 2-continued

| | Composition | | | (tablet) Amount of Chlorine or Nitrogen Chloride Gas mg | | Dissolution Rate g/30 g/ 8 hr | Active Chlorine Concentration 8 Hrs. After ppm | Appearance |
|---|---|---|---|---|---|---|---|---|
| | Chloroisocyanuric Acid g | | Aluminum Sulfate Salt g | Dry State | Wet State | | | |
| | | | 12 hydrate (powder) | | | | | but dissolved uniformly. |
| Ex. 15 | TCCA | 27.0 | Potassium alum 12 hydrate (powder) | 3.0 0.07 | — | 9.1 | 5.1 | No collapsed but dissolved uniformly. |
| Ex. 16 | TCCA | 21.0 | Sodium alum 12 hydrate (powder) | 9.0 0.08 | 9.0 | 14.4 | 6.3 | No collapsed but dissolved uniformly. |
| Ex. 17 | TCCA | 27.0 | Sodium alum 12 hydrate (powder) | 3.0 0.10 | — | 9.6 | 5.4 | No collapsed but dissolved uniformly. |
| Ex. 18 | TCCA | 21.0 | Sodium sulfate 18 hydrate (powder) | 9.0 0.08 | 8.7 | 24.2 | 10.6 | No collapsed but dissolved uniformly. |
| Ex. 19 | TCCA | 27.0 | Sodium sulfate 18 hydrate (powder) | 3.0 0.09 | — | 13.1 | 7.4 | No collapsed but dissolved uniformly. |
| Ex. 20 | DCCA | 21.0 | Potassium alum 12 hydrate (powder) | 9.0 0.04 | 2.0 | 6.9 | 3.1 | No collapsed but dissolved uniformly. |
| Ex. 21 | DCCA | 21.0 | Sodium sulfate 18 hydrate (powder) | 9.0 0.06 | — | 7.9 | 3.6 | No collapsed but dissolved uniformly. |
| Ex. 22 (*1) | TCCA | 21.0 | Potassium alum 12 hydrate (powder) | 6.0 0.06 | 9.8 | 14.0 | 6.4 | No collapsed but dissolved uniformly. |
| Ex. 23 (*1) | TCCA | 21.0 | Sodium sulfate 18 hydrate (power) | 6.0 0.08 | 10.2 | 19.6 | 8.2 | No collapsed but dissolved uniformly. |
| Comp. Ex. 9 | TCCA | 30.0 | — | 0.24 | 22.9 | 3.7 | 2.3 | No collapsed but dissolved uniformly. |
| Comp. Ex. 10 | DCCA | 30.0 | — | 0.17 | 6.0 | 1.6 | 0.8 | No collapsed but dissolved uniformly. |
| Comp. Ex. 11 | TCCA | 21.0 | Sodium sulfate 10 hydrate (powder) | 9.0 4.1 | 20.3 | | | cracking |
| Comp. Ex. 12 | TCCA | 21.0 | Sodium primary phosphate 2 hydrate (powder) | 9.0 1.9 | — | | | " |
| Comp. Ex. 13 | TCCA | 21.0 | Magnesium sulfate 7 hydrate (powder) | 9.0 5.3 | 16.5 | | | " |
| Comp. Ex. 14 | TCCA | 21.0 | Magnesium chloride 6 hydrate (powder) | 9.0 ≧50 | — | | | collapse |
| Comp. Ex. 15 | TCCA | 21.0 | Sodium carbonate 7 hydrate (powder) | 9.0 9.5 | ≧50 | | | " |
| Comp. Ex. 16 | TCCA | 21.0 | Sodium tetraborate 10 hydrate (powder) | 9.0 6.3 | — | | | " |
| Comp. Ex. 17 | TCCA | 21.0 | Potassium alum anhydride (powder) | 9.0 0.17 | 12.4 | | | " |
| Comp. Ex. 18 | TCCA | 21.0 | Sodium alum anhydride (powder) | 9.0 0.22 | — | | | " |
| Comp. | TCCA | 21.0 | Aluminum sulfate | 9.0 0.14 | — | | | " |

TABLE 2-continued

| | Composition (tablet) | | Amount of Chlorine or Nitrogen Chloride Gas mg | | Dissolution Rate g/30 g/ 8 hr | Active Chlorine Concentration 8 Hrs. After ppm | Appearance |
|---|---|---|---|---|---|---|---|
| | Chloroisocyanuric Acid g | Aluminum Sulfate Salt g | Dry State | Wet State | | | |
| Ex. 19 | | anhydride (powder) | | | | | |

(*1) 3.0 g of orthoboric acid was additionally added.
TCCA: trichloroisocyanuric acid (granule)
DCCA: dichloroisocyanuric acid (granule)

While the present invention has been described in detail and with reference to specific embodiments thereof, it will be apparent to one skilled in the art that various changes and modifications can be made therein without departing from the spirit and scope thereof.

What is claimed is:

1. A chloroisocyanuric acid composition having stability during storage comprising trichloroisocyanuric acid and/or dichloroisocyanuric acid characterized by formulating, as a main component, 1 to 200 parts by weight of at least one aluminum sulfate salt selected from hydrated aluminum sulfate ($Al_2(SO_4)_3 \cdot XH_2O$, $X=6$ to 18), hydrated potassium alum ($KAl(SO_4)_2 \cdot XH_2O$, $X=6$ to 12) and hydrated sodium alum ($NaAl(SO_4)_2 \cdot XH_2O$, $X=6$ to 12) in 100 parts by weight of said trichloroisocyanuric acid and/or dichloroisocyanuric acid.

2. A chloroisocyanuric acid composition as claimed in claim 1, wherein said aluminum sulfate salt is selected from aluminum sulfate 18 hydrate, potassium alum 12 hydrate and sodium alum 12 hydrate.

3. A chloroisocyanuric acid composition as claimed in claim 1, which is prepared into a form of a tablet.

4. A chloroisocyanuric acid composition as claimed in claim 2, which is prepared into a form of a tablet.

* * * * *